US012653709B2

(12) United States Patent
Moon et al.

(10) Patent No.: US 12,653,709 B2
(45) Date of Patent: Jun. 16, 2026

(54) STENT DELIVERY ASSEMBLY

(71) Applicants: GENOSS CO., LTD., Suwon-si (KR); MDSYNOD CO., LTD., Seongnam-si (KR)

(72) Inventors: Eun Ju Moon, Seongnam-si (KR); Sung Min Chung, Suwon-si (KR); Su Jo Jung, Suwon-si (KR); Seung-Jea Tahk, Seongnam-si (KR)

(73) Assignees: GENOSS CO., LTD., Seongnam-si (KR); MDSYNOD CO., LTD., Seongnam-si (KR)

( * ) Notice: Subject to any disclaimer, the term of this patent is extended or adjusted under 35 U.S.C. 154(b) by 1027 days.

(21) Appl. No.: 17/775,346

(22) PCT Filed: Jan. 26, 2022

(86) PCT No.: PCT/KR2022/001350
§ 371 (c)(1),
(2) Date: May 9, 2022

(87) PCT Pub. No.: WO2022/182005
PCT Pub. Date: Sep. 1, 2022

(65) Prior Publication Data
US 2023/0041446 A1 Feb. 9, 2023

(30) Foreign Application Priority Data

Feb. 25, 2021 (KR) ......................... 10-2021-0025497

(51) Int. Cl.
*A61F 2/958* (2013.01)
*A61F 2/954* (2013.01)
(Continued)

(52) U.S. Cl.
CPC .............. *A61F 2/958* (2013.01); *A61F 2/954* (2013.01); *A61F 2002/821* (2013.01); (Continued)

(58) Field of Classification Search
CPC ................ A61F 2002/821; A61F 2/954; A61F 2/958–2002/9586
See application file for complete search history.

(56) References Cited

U.S. PATENT DOCUMENTS

| 10,470,905 B2 | 11/2019 | Yang et al. |
| 2005/0171597 A1 | 8/2005 | Boatman et al. |
| | (Continued) | |

FOREIGN PATENT DOCUMENTS

| JP | 2007-130469 A | 5/2007 |
| JP | 2009-505742 A | 2/2009 |
| | (Continued) | |

OTHER PUBLICATIONS

International Search Report Corresponding to PCT/KR2022/001350 mailed May 9, 2022.
(Continued)

*Primary Examiner* — Rebecca S Preston
(74) *Attorney, Agent, or Firm* — Secant, IP, PLLC

(57) ABSTRACT

The present invention provides a stent delivery assembly including: a catheter including a shaft having a proximal end and a distal end, and a balloon provided closer to the proximal end than the distal end on the shaft; and a stent having a tubular shape, and coupled to the balloon to surround an outer circumferential surface of the balloon, wherein the balloon includes a main body having a first end and a second end, the stent is located to be biased towards the first end, such that the main body includes a preferential inflation region exposed to the outside between the second end and the stent, the main body is formed to extend with a diameter that is constant from the first end to the second end, and while the balloon is inflated, a portion of the stent close to the preferential inflation region is inflated in a tapered (Continued)

shape by a force caused when the preferential inflation region is preferentially inflated.

7 Claims, 3 Drawing Sheets

(51) Int. Cl.

| | | |
|---|---|---|
| A61F 2/82 | (2013.01) | |
| A61F 2/90 | (2013.01) | |
| A61M 25/10 | (2013.01) | |

(52) U.S. Cl.
CPC ......... *A61F 2/90* (2013.01); *A61F 2230/0067* (2013.01); *A61F 2230/0069* (2013.01); *A61F 2250/0039* (2013.01); *A61M 2025/1059* (2013.01)

(56)                References Cited

U.S. PATENT DOCUMENTS

| | | |
|---|---|---|
| 2006/0135985 A1 | 6/2006 | Cox et al. |
| 2007/0067011 A1 | 3/2007 | Krolik et al. |
| 2007/0106364 A1 | 5/2007 | Buzzard et al. |
| 2009/0177259 A1 | 7/2009 | Ning et al. |
| 2009/0259288 A1 | 10/2009 | Wijay et al. |
| 2011/0190867 A1 | 8/2011 | Vonderwalde et al. |
| 2014/0046431 A1* | 2/2014 | Papp ....................... A61F 2/958 623/1.16 |
| 2014/0100647 A1* | 4/2014 | Bourang ................. A61F 2/958 623/1.12 |
| 2019/0133800 A1 | 5/2019 | Krolik |
| 2020/0383780 A1 | 12/2020 | Chang et al. |

FOREIGN PATENT DOCUMENTS

| | | | |
|---|---|---|---|
| JP | 2012-500673 A | 1/2012 | |
| JP | 2020-512110 A | 4/2020 | |
| KR | 10-2315566 B1 | 10/2021 | |

OTHER PUBLICATIONS

Written Opinion Corresponding to PCT/KR2022/001350 mailed May 9, 2022.

Japan Patent Application 2022-538464, Notice of Reasons for Refusal dated Jul. 11, 2023.

Europe Patent Application 22 71 7054, Extended European Search Report dated Dec. 8, 2023.

\* cited by examiner 155          117

150

113     115                                          117

150                    155

EVALUATION BASED ON LENGTH OF
PREFERENTIAL INFLATION REGION

------ ANGLE OF TAPERED PORTION        —— PROBABILITY OF POSITIONAL SHIFT OF STENT

STENT DELIVERY ASSEMBLY

TECHNICAL FIELD

The present invention relates to an assembly for delivering a stent to a specific location in a blood vessel.

BACKGROUND ART

In a typical stent delivery assembly, a stent is crimped on a balloon, such that the stent inflated according to inflation of the balloon expands a narrow blood vessel after the stent approaches a target lesion.

For an ostial lesion at an inlet of a blood vessel or a bifurcation lesion at a portion where a blood vessel is branched, the stent needs to be accurately located at an ostium of the blood vessel and deformed according to a shape of the blood vessel. Such a portion is difficult to visually identify through angiography, and a cardiovascular vessel shifts according to a heartbeat. Thus, it is very difficult for an operator to accurately locate a proximal portion of the stent into the ostium of the blood vessel during a medical procedure.

To this end, various types of stents and stent delivery assemblies have been developed, but there has not yet been provided a technique for manufacturing the stents and the stent delivery assemblies in a convenient and effective way. For example, there is a technique for manufacturing a balloon of a catheter in a tapered form, it is difficult to manufacture the balloon in a specific shape.

DISCLOSURE

Technical Problem

An object of the present disclosure is to provide a stent delivery assembly enabling a balloon to be expanded after being accurately positioned to correspond to an ostial lesion or a bifurcation lesion of a blood vessel while making it easy to manufacture the balloon.

Technical Solution

According to an exemplary embodiment of the present invention, there is provided a stent delivery assembly including: a catheter including a shaft having a proximal end and a distal end, and a balloon provided closer to the proximal end than the distal end on the shaft; and a stent having a tubular shape, and coupled to the balloon to surround an outer circumferential surface of the balloon, wherein the balloon includes a main body having a first end and a second end, the stent is located to be biased towards the first end, such that the main body includes a preferential inflation region exposed to the outside between the second end and the stent, the main body is formed to extend with a single inner space having a single diameter that is constant in an entire section from the first end to the second end, an entire region from one end to the other end of the stent is located within the entire section of the balloon, which is formed to extend with the constant diameter between the first end and the second end, to correspond to the balloon, the shaft includes a lumen communicating with the single inner space, and in a process in which the balloon is inflated by a fluid supplied into the single inner space through the lumen, a portion of the stent close to the preferential inflation region is inflated in a tapered shape by a force caused when the preferential inflation region of the balloon is preferentially inflated as compared to a delayed inflation region of the balloon surrounded by the stent and subjected to resistance to the inflation.

Here, the first end may be located closer to the proximal end of the shaft than the second end.

Here, a length of the preferential inflation region may be determined within a range of 3 to 7 mm.

Here, a length of the preferential inflation region may be determined within a range of 3 to 6 mm.

According to another exemplary embodiment of the present invention, there is provided a stent delivery assembly including: a catheter including a shaft having a proximal end and a distal end, and a balloon provided closer to the proximal end than the distal end on the shaft; and a stent having a tubular shape, and coupled to the balloon to surround an outer circumferential surface of the balloon, wherein the balloon includes a main body having a first end and a second end, the stent is located to be biased towards the first end, such that the main body includes a preferential inflation region exposed to the outside between the second end and the stent, the main body is formed to extend with a single inner space having a diameter that is constant from the first end to the second end, and in a process in which the balloon is inflated, a portion of the stent close to the preferential inflation region is inflated in a tapered shape by a force caused when the preferential inflation region of the balloon is preferentially inflated as compared to a delayed inflation region of the balloon surrounded by the stent and subjected to resistance to the inflation.

Here, an entire region from one end to the other end of the stent may be located within the entire section of the balloon, which is formed to extend with the constant diameter between the first end and the second end, to correspond to the balloon.

Here, the first end may be located closer to the proximal end of the shaft than the second end.

Here, a length of the preferential inflation region may be determined within a range of 3 to 6 mm.

According to another exemplary embodiment of the present invention, there is provided a stent delivery assembly including: a catheter including a shaft having a proximal end and a distal end, and a balloon provided closer to the proximal end than the distal end on the shaft; and a stent having a tubular shape, and coupled to the balloon to surround an outer circumferential surface of the balloon, wherein the balloon includes a main body having a first end and a second end, the stent is located to be biased towards the first end, such that the main body includes a preferential inflation region exposed to the outside between the second end and the stent, the main body is formed to extend with a diameter that is constant from the first end to the second end, and while the balloon is inflated, a portion of the stent close to the preferential inflation region is inflated in a tapered shape by a force caused when the preferential inflation region is preferentially inflated.

Here, the shaft may further include a lumen communicating with an inner space of the main body, and the balloon may be inflated by a fluid supplied into the inner space through the lumen.

Here, the main body may further include a delayed inflation region surrounded by the stent, and in a process in which the balloon is inflated, the preferential inflation region may be preferentially inflated while the delayed inflation region is subjected to resistance to the inflation by the stent.

Advantageous Effects

In the stent delivery assembly configured as described above according to the present invention, the balloon is included in the catheter, and the stent is disposed to surround the balloon. When the balloon is divided into a region surrounded by the stent and a preferential inflation region that is not surrounded by the stent and is exposed to the outside, the preferential inflation region is located to be biased toward the second end of the main body of the balloon, and the main body including the preferential inflation region extends with a constant diameter. Therefore, the balloon is easy to process. In addition, while the balloon is inflated, a portion of the stent close to the preferential inflation region can be inflated in a tapered form by a force caused when the preferential inflation region is preferentially inflated.

BEST MODE FOR INVENTION

Figure 1:
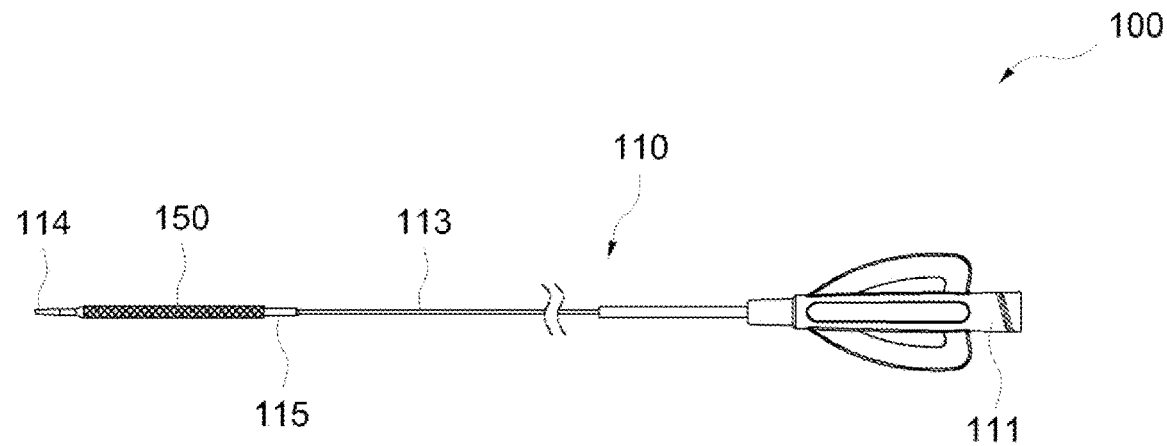
FIG. 1 is a conceptual perspective view showing a stent delivery assembly 100 according to an exemplary embodiment of the present invention.

Hereinafter, a stent delivery assembly according to a preferred exemplary embodiment of the present invention will be described in detail with reference to the accompanying drawings. Throughout the present specification, the same or similar reference numerals denote the same or similar components even in different exemplary embodiments. Once the same or similar components are described, the description thereof will not be repeated.

FIG. 1 is a conceptual perspective view showing a stent delivery assembly 100 according to an exemplary embodiment of the present invention.

Referring to FIG. 1, the stent delivery assembly 100 may include a catheter 110 and a stent 150.

First, the catheter 110 may have a hub 111, a shaft 113, and a balloon 115.

The hub 111 is a hollow cylinder. The hub 111 is shaped to be grabbed in an operator's hand. In terms of material, the hub 111 may be made of a plastic-based material.

The shaft 113, which is a portion to be inserted into a blood vessel, may have a tube-like shape. A proximal end 114, which is one end of the shaft 113, is an inserting proximal end for insertion into a blood vessel, and a distal end, which is the other end of the shaft 113, is a fixing distal end for fixation to the hub 111. The shaft 113 may have a lumen formed therein. A portion of the shaft 113 close to the proximal end 114, which is a portion to be inserted into a blood vessel having many curves, for example, in a heart, may be made of a high-ductility material to be bent to correspond to the curves.

The balloon 115 may be provided at a location close to the proximal end 114 of the shaft 113. The balloon 115 is formed of an elastic material to be inflated by a fluid supplied through the lumen. When the supply of the fluid is stopped or withdrawn, the balloon 115 may be deflated back. Only a single lumen is formed in the shaft 113 with respect to a single inner space of the balloon 115 to supply a single fluid. Therefore, the stent delivery assembly is suitable for use in a cardiovascular vessel. This is because the catheter used for the cardiovascular vessel needs to have excellent flexibility to reach a deep lesion, and the catheter having a smaller cross-sectional area is more advantageous when passing through a narrow lesion. It is also because the balloon needs to be deflated or inflated during a medical procedure within a short period of time for the reason that the cardiovascular vessel cannot be blocked for a long period of time. In addition, as another advantage of the formation of only the single lumen in the shaft 113 with respect to the single inner space of the balloon 115 to supply the single fluid, an operator only needs to operate one inflation/deflation device.

Next, the stent 150 is a structure to be inserted into a blood vessel to widen a cross-sectional area of blood flow in the blood vessel. In the stent 150, struts extending in a zigzag form are connected to each other to form an inflatable pipe as a whole (see the photograph of FIG. 4). Furthermore, the stent 150 may be formed of a cobalt alloy material.

The stent 150 is shrunk in a state where it surrounds an outer circumferential surface of the balloon 115, and coupled to the balloon 115 in a crimped manner. The stent 150 may have a smaller length than the balloon 115.

Figure 2:
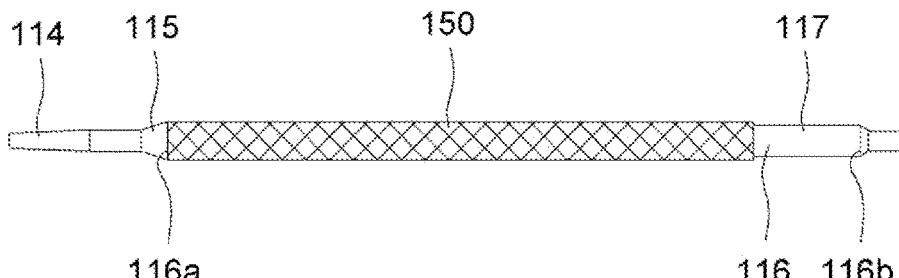
FIG. 2 is a conceptual enlarged perspective view showing a portion where a balloon 115 and a stent 150 are coupled to each other of FIG. 1.

Now, a coupling relationship between the balloon 115 and the stent 150 will be described in detail with reference to FIG. 2. FIG. 2 is a conceptual enlarged perspective view showing the balloon 115 and the stent 150 of FIG. 1.

Referring to FIG. 2, the balloon 115 is formed to extend along a longitudinal direction of the shaft 113. The balloon 115 has a main body 116. A first end 116*a*, which is one end of the main body 116, is located close to the proximal end 114, and a second end 116*b*, which is the other end of the main body 116, is located closer to the hub 111 than the first end 116*a*. The balloon 115 has a diameter that is kept constant from the first end 116*a* to the second end 116*b*. The main body 116 has a single inner space from the first end 116*a* to the second end 116*b*. This is advantageous in making it simple to manufacture the balloon 115 by injection molding and manufacture the shaft 113 having a lumen.

The main body 116 is not fully covered by the stent 150. Furthermore, the stent 150 is located to be biased towards the first end 116*a*. Thus, a region of the main body 116 of the balloon 115 that is not covered by the stent 150, in other words, a region between the stent 150 and the second end 116*b*, is exposed to the outside. The region exposed to the outside may be referred to as a preferential inflation region 117.

Concerning the preferential inflation region 117, results of experiments for its functions will be described with reference to FIGS. 3 to 6.

Figure 3:
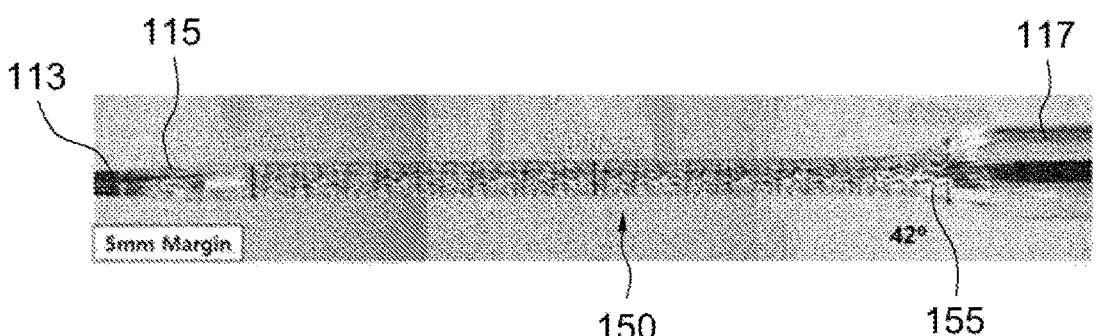
FIG. 3 is a photograph showing a result of an experiment in which a preferential inflation region 117 has a length of 5 mm.
Figure 4:
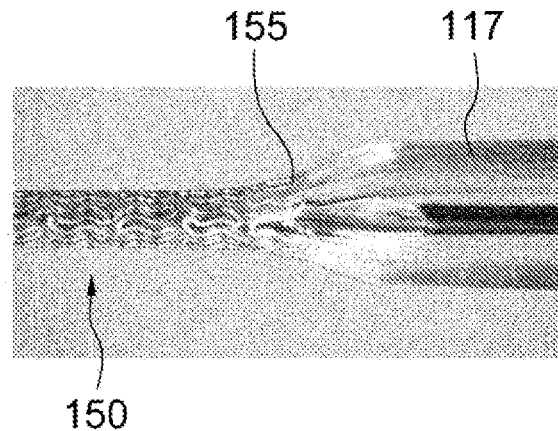
FIG. 4 is an enlarged photograph mainly showing a tapered portion 155 of FIG. 3.

First, FIG. 3 is a photograph showing a result of an experiment in which the preferential inflation region 117 has a length of 5 mm, and FIG. 4 is an enlarged photograph mainly showing a tapered portion 155 of FIG. 3.

Referring to FIGS. 3 and 4, when the balloon 115 is inflated by injecting a fluid into the single inner space of the balloon 115 through the lumen, the preferential inflation region 117 of the balloon 115 is preferentially inflated. This is because a portion (a delayed inflation region) of the balloon 115 surrounded by the stent 150 is subjected to resistance by the stent 150, whereas the preferential inflation region 117 does not have such a constraint.

A tapered portion 155 having a diameter that increases toward an end of the stent 150 is formed in an end region of the stent 150 adjacent to the preferential inflation region 117 by a force caused when the preferential inflation region 117 is preferentially inflated. Thus, when a diameter of a central portion of the stent 150 is 1.04 mm, a diameter of an edge of the tapered portion 155 is 1.88 mm. As a result, an initial angle of the tapered portion 155 reaches 42°. Such an initial angle enables an operator to perceive that the stent 150 has just become caught at an opening portion of a blood vessel or an inlet portion of a branched blood vessel, thereby accurately determining a location of the stent 150 in an easier way by slightly pushing the delivery system.

Figure 5:
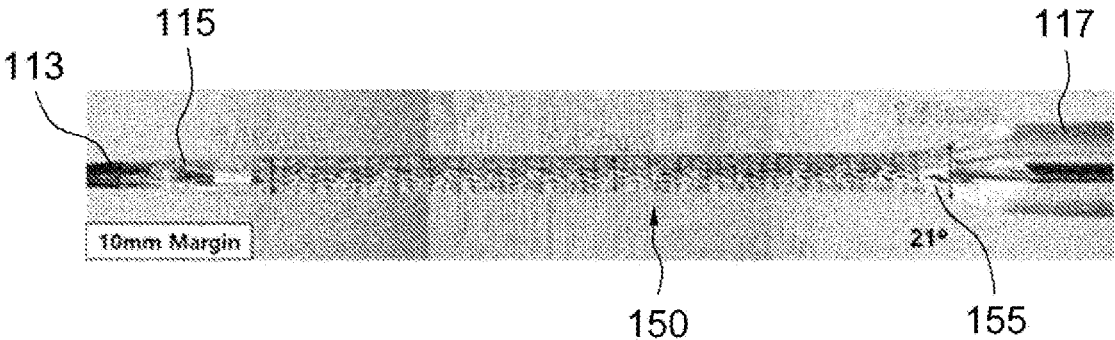
FIG. 5 is a photograph showing a result of an experiment in which a preferential inflation region 117 has a length of 10 mm.

Next, FIG. 5 is a photograph showing a result of an experiment in which the preferential inflation region 117 has a length of 10 mm.

Referring to FIG. 5, when the balloon 115 is inflated, the preferential inflation in the preferential inflation region 117 forms a tapered portion 155 of which an initial angle is 21°. It can be seen that the initial angle of the tapered portion 155 is smaller than that in the above-described case where the preferential inflation region 117 is 5 mm long.

This is because, as the length of the preferential inflation region 117 increases, the force caused when the preferential inflation region 117 is inflated acts gently on the tapered portion 155 of the stent 150.

Figure 6:
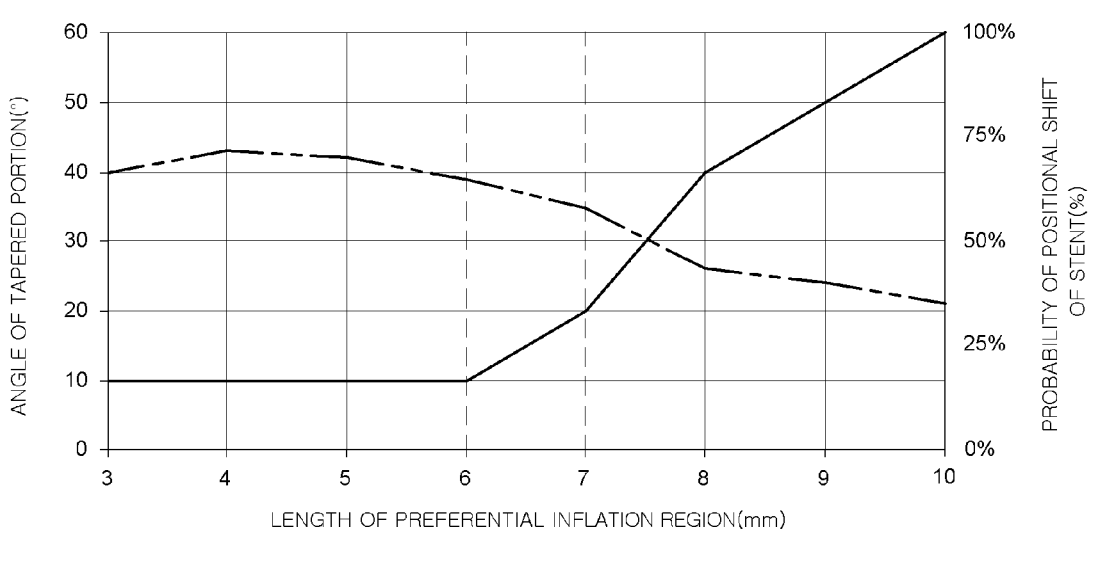
FIG. 6 is a graph collectively showing experimental results based on a length of the preferential inflation region 117.

Now, these experimental results will be collectively reviewed with reference to FIG. 6. FIG. 5 is a graph showing experimental results for the preferential inflation region 117.

Referring to FIG. 6 (together with FIGS. 1 to 5), the results are shown only for specimens whose preferential inflation regions 117 have lengths starting from 3 mm and finally reaching 10 mm in 1 mm increments. Six specimens were tested for each length of the preferential inflation region 117. When the length of the preferential inflation region 117 was less than 3 mm, the tapered portion 155 was not formed in the stent 150 or was formed intermittently. Thus, specimens having a length of less than 3 mm are excluded from the result graph.

The stent 150 having a length of 18 mm was used. The length of the stent 150 may be selected in the range of half to double of 18 mm, which is the adopted length. Although the length of the stent 150 changes, the appropriate length of the preferential inflation region 117 does not change. The balloon 115, specifically the main region 116, was manufactured to have a length obtained by adding the length of the preferential inflation region 117 to the length of the stent 150.

A first experiment is to measure an angle of the tapered portion 155 of the stent 150 while the balloon 115 is inflated by injecting the fluid into the balloon 115. This is because the preferential inflation region 117 is preferentially inflated when the balloon 115 is inflated, and the tapered portion 155 is formed in one end portion of the stent 150 by a force generated from the preferential inflation region 117.

As a result of the experiment, the angle of the tapered portion 155 depending on the length of the preferential inflation region 117 is as shown in the following table.

TABLE 1

| Length (mm) of Preferential Inflation Region 117 | 3 | 4 | 5 | 6 | 7 | 8 | 9 | 10 |
|---|---|---|---|---|---|---|---|---|
| Angle (°) of Tapered Portion 155 | 40 | 43 | 42 | 39 | 35 | 26 | 24 | 21 |

From the table above, it can be seen that the angle of the tapered portion 155 slightly increases when the length of the preferential inflation region 117 increases from 3 mm to 4 mm, but the angle of the tapered portion 155 decreases as the length of the preferential inflation region 117 increases from at least 4 mm. In particular, it can be seen that the angle of the tapered portion 155 decreases in a largest degree by 9° in a section where the length of the preferential inflation region 117 increases from 7 mm to 8 mm. In the other sections, the angle of the tapered portion 155 generally decreases by 2° to 4°. A decrease width in a section where the length of the preferential inflation region 117 increases from 7 mm to 8 mm is two times a maximum decrease width in the other sections.

In a second experiment, a specimen was tested for a probability that the specimen might be a defective specimen in which the stent 150 was pushed in a direction toward the proximal end 114 by the force generated from the preferential inflation region 117, and is provided at an undesired location. Since the six specimens were tested for each length of the preferential inflation region 117, the number of specimens where positional shifts occurred among the six specimens was determined to calculate a probability of shift. The results are shown in the following table.

TABLE 2

| Length (mm) of Preferential Inflation Region 117 | 3 | 4 | 5 | 6 | 7 | 8 | 9 | 10 |
|---|---|---|---|---|---|---|---|---|
| The Number of Stents 150 That Have Shifted | 1 | 1 | 1 | 1 | 2 | 4 | 5 | 6 |
| Probability of Shift of Stent 150 | 17 | 17 | 17 | 17 | 33 | 67 | 83 | 100 |

When the length of the preferential inflation region 117 is in the range of 3 mm to 6 mm, a probability of shift of the stent 150 is constant as 17%. However, when the length of the preferential inflation region 117 increases to 7 mm, the probability of shift of the stent 150 increases doubly, and when the length of the preferential inflation region 117 increases from 7 mm to 8 mm, the probability of shift of the stent 150 increases doubly once more. When the length of the preferential inflation region 117 increases finally to 10 mm, the probability of shift of the stent 150 reaches 100%.

In the graph of FIG. 5, both the angle of the tapered portion 155 and the probability of shift of the stent 150 described above are shown. Referring to FIG. 5, the length of the preferential inflation region 117 may be preferably determined within the range of 3 to 7 mm. This is because it is possible to avoid a section in which the angle of the tapered portion 155 sharply decreases from 35° to 26° as the length of the preferential inflation region 117 increases from 7 mm to 8 mm, that is, by about twice the decreases in the other sections. Furthermore, in terms of the probability of shift of the stent 150, it is also possible to avoid a section where the probability of shift of the stent 150 greatly increases from 33% to 67%.

More preferably, the length of the preferential inflation region 117 may be determined within the range of 3 to 6 mm. This is because, especially in terms of the probability of shift of the stent 150, it is possible to avoid a section where the probability of shift of the stent 150 increases doubly from 17% to 33% for the first time. When the preferential inflation region 117 is 6 mm long, it is also possible to maintain the tapered portion 155 at a wide angle, i.e. 39°.

The above-described stent delivery assembly is not limited to the configuration and operation method in the exemplary embodiments described above. The above-described exemplary embodiments may also be combined together either partially or entirely in a selective manner to make various modifications.

INDUSTRIAL APPLICABILITY

The present invention is industrially applicable in the stent delivery assembly manufacturing field.

The invention claimed is:

1. A stent delivery assembly comprising:

a catheter including a shaft having a proximal end and a distal end, and a balloon provided closer to the proximal end than the distal end on the shaft; and a stent having a tubular shape, and coupled to the balloon to surround an outer circumferential surface of the balloon, wherein the balloon includes a main body having a first end and a second end, the stent is located to be biased towards the first end, such that the main body of the balloon includes a preferential inflation region that is not surrounded by the stent in a region between the second end and the stent and a delayed inflation region surrounded by the stent, the main body is formed to extend in an uninflated state with a diameter that is constant from the first end to the second end, the stent delivery assembly is configured such that while the balloon is inflated, a portion of the stent surrounding a distal end of the delayed inflation region close to the preferential inflation region is inflated to form a tapered shape portion by a force caused when the preferential inflation region is preferentially inflated, a length of the preferential inflation region is within a range of 3 mm to 6 mm, and an initial angle of the tapered shape portion is inclined within a range of 39° to 43° from a central axis of the catheter.

2. The stent delivery assembly of claim 1, wherein the shaft further includes a lumen communicating with an inner space of the main body, and the balloon is configured to be inflated by a fluid supplied into the inner space through the lumen.

3. The stent delivery assembly of claim 1, wherein in a process in which the balloon is inflated, the preferential inflation region is preferentially inflated while the delayed inflation region is subjected to resistance to inflation by the stent.

4. A stent delivery assembly comprising:

a catheter including a shaft having a proximal end and a distal end, and a balloon provided closer to the proximal end than the distal end on the shaft; and a stent having a tubular shape, and coupled to the balloon to surround an outer circumferential surface of the balloon, wherein the balloon includes a main body having a first end and a second end, the stent is located to be biased towards the first end, such that the main body of the balloon includes a preferential inflation region that is not surrounded by the stent in a region between the second end and the stent and a delayed inflation region surrounded by the stent, the main body is formed to extend in an uninflated state with a single inner space having a diameter that is constant from the first end to the second end, in a process in which the balloon is inflated, a portion of the stent surrounding a distal end of the delayed inflation region close to the preferential inflation region is inflated to form a tapered shape portion by a force caused when the preferential inflation region of the balloon is preferentially inflated as compared to a proximal end of the delayed inflation region of the balloon subjected to resistance to inflation, a length of the preferential inflation region is within a range of 3 mm to 6 mm, and an initial angle of the tapered shape portion is inclined within a range of 39° to 43° from a central axis of the catheter.

5. The stent delivery assembly of claim 4, wherein the first end is located closer to the proximal end of the shaft than the second end.

6. A stent delivery assembly comprising:

a catheter including a shaft having a proximal end and a distal end, and a balloon provided closer to the proximal end than the distal end on the shaft; and a stent having a tubular shape, and coupled to the balloon to surround an outer circumferential surface of the balloon, wherein the balloon includes a main body having a first end and a second end, the stent is located to be biased towards the first end, such that the main body of the balloon includes a preferential inflation region that is not surrounded by the stent in a region between the second end and the stent and a delayed inflation region surrounded by the stent, the main body is formed to extend in an uninflated state with a single inner space having a single diameter that is constant from the first end to the second end, the shaft includes a lumen communicating with the single inner space, in a process in which the balloon is inflated by a fluid supplied into the single inner space through the lumen, a portion of the stent surrounding a distal end of the delayed inflation region close to the preferential inflation region is inflated to form a tapered shape portion by a force caused when the preferential inflation region of the balloon is preferentially inflated as compared to a proximal end of the delayed inflation region of the balloon subjected to resistance to inflation, a length of the preferential inflation region is within a range of 3 mm to 6 mm, and an initial angle of the tapered shape portion is inclined within a range of 39° to 43° from a central axis of the catheter.

7. The stent delivery assembly of claim 6, the first end is located closer to the proximal end of the shaft than the second end.

* * * * *